United States Patent [19]

Diamond et al.

[11] 4,363,808

[45] Dec. 14, 1982

[54] N-(3-PHENOXY-2-HYDROXYPROPYL)BEN-ZIMIDAZOLE-1-ALKANAMINES

[75] Inventors: Julius Diamond, Mountain Lakes; Ronald A. Wohl, Morris Plains, both of N.J.

[73] Assignee: Berlex Laboratories, Inc., Cedar Knolls, N.J.

[21] Appl. No.: 261,331

[22] Filed: May 7, 1981

Related U.S. Application Data

[63] Continuation-in-part of Ser. No. 120,416, Feb. 11, 1980, abandoned.

[30] Foreign Application Priority Data

Feb. 10, 1981 [EP] European Pat. Off. ........ 81730014.8
Feb. 10, 1981 [IE] Ireland .................................. 250/81
Feb. 12, 1981 [JP] Japan ................................... 56-1955

[51] Int. Cl.³ ................ A61K 31/535; C07D 473/00; C07D 471/04

[52] U.S. Cl. ............... 424/248.51; 424/253; 424/256; 424/258; 424/263; 424/270; 424/273 B; 544/118; 544/127; 544/134; 544/277; 546/118; 546/165; 546/271; 548/181; 548/327; 548/333

[58] Field of Search ............. 548/333, 327, 181; 546/118, 165, 271; 544/277, 118, 127, 134; 424/273 B, 258, 253, 256, 248.51, 263, 270

[56] References Cited

U.S. PATENT DOCUMENTS

4,035,369  7/1977  Vandenberk et al. .......... 548/305 X
4,179,505  12/1979  Raeymaekers et al. ........ 548/305 X

FOREIGN PATENT DOCUMENTS

859415  4/1978  Belgium .

Primary Examiner—Richard A. Schwartz
Attorney, Agent, or Firm—Elizabeth A. Bellamy; John L. White; I. William Millen

[57] ABSTRACT

3-Phenoxy-2-hydroxypropylamines having an N-benzimidazolylalkyl substituent and similar compounds are described herein. They are obtained by the reaction of the appropriate imidazole-1-alkanamine with an epoxide, and they are useful primarily as β-adrenergic blocking agents.

7 Claims, No Drawings

N-(3-PHENOXY-2-HYDROXYPROPYL)BEN-ZIMIDAZOLE-1-ALKANAMINES

CROSS REFERENCE TO RELATED APPLICATIONS

This application is a continuation-in-part of application Ser. No. 120,416 filed Feb. 11, 1980, now abandoned.

BACKGROUND OF THE INVENTION

The present invention relates to novel compounds which are N-(3-phenoxy-2-hydroxypropyl)benzimidazole-1alkanamines and related compounds.

SUMMARY OF THE INVENTION

In a composition aspect, this invention relates to compounds of the general formula

Z—Alk—NH—CH$_2$—CH(OR)—CH$_2$—O—A wherein Alk is an alkylene goup containing 2 to 6 carbon atoms; Z is a bicyclic imidazole with the attachment through a nitrogen of the imidazole ring; A is phenyl optionally substituted with one or more groups or with an additional carbocyclic or heterocyclic ring fused thereto or A can be cyanopyridyl, carboxypyridyl, carbamoylpyridyl, alkoxycarbonylpyridyl, thiazolyl or morpholinothiadiazolyl; and R is hydrogen or an acyl group; and the pharmaceutically acceptable acid addition salts thereof.

DETAILED DISCUSSION

More particularly, the alkylene group Alk separates the atoms attached thereto by at least two carbon atoms and can be exemplified by ethylene, trimethylene, 1-methyl-1,2-ethanediyl, tetramethylene, 1-methyl-1,3-propanediyl, 2-methyl-1,3-propanediyl, pentamethylene, 1-methyl-1,4-butanediyl and 1,3-dimethyl-1,4-butanediyl. A particularly preferred Alk group is trimethylene.

Z represents an imidazole of the structure

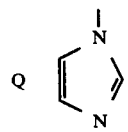

wherein Q< indicates a benzene ring fused to the imidazole ring. The benzene ring can be partially saturated as in tetrahydrobenzene or it can contain one or two nitrogens as in pyridine or pyrimidine. In addition, when Q indicates a benzene ring, the resulting benzimidazole can contain further substituents, such as a 1-4 C alkyl, in the 2-position or the 4 to 7-positions. More particularly, Z represents 1-benzimidazolyl; methyl-1-benzimidazolyl such as 2-methyl-1-benzimidazolyl, 4-methyl-1-benzimidazolyl, 5-methyl-1-benzimidazolyl, 6-methyl-1-benzimidazolyl, 7-methyl-1-benzimidazolyl; 4,5,6,7-tetrahydro-1-benzimidazolyl, 1H-imidazo[4,5-b]pyridin-1-yl, 1H-imidazo[4,5-c]pyridin-1-yl or (9H)-9-purinyl. Particularly preferred are those compounds in which Z is 1-benzimidazolyl or methyl-1-benzimidazolyl with the compound in which Z is 1-benzimidazolyl being most particularly preferred.

A can be phenyl, tolyl, hydroxyphenyl, halophenyl, nitrophenyl, trifluoromethylphenyl, cyanophenyl, cyclopentylphenyl, allylphenyl, allyloxyphenyl, dimethoxyphenyl; carbamoylmethylphenyl of the formula

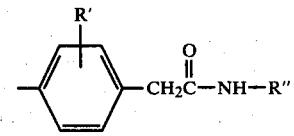

wherein R' is hydrogen, methyl or halogen and R" is hydrogen or lower alkyl containing up to 4 carbon atoms; carboxymethylphenyl, (lower alkyl)oxycarbonylmethylphenyl wherein lower alkyl contains up to 4 carbon atoms; (acid amido)phenyl and (acid amido alkyl)-phenyl of the formula

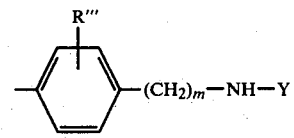

wherein m is 0-2, R''' is hydrogen, methyl, acetyl or halogen and Y is

$\overset{O}{\underset{\|}{C}}$—(lower alkyl), and —$\overset{O}{\underset{\|}{C}}$—O—(lower alkyl)

in which lower alkyl contains up to 4 carbon atoms and methylsulfonyl; (lower alkyl)oxyalkylphenyl of the formula

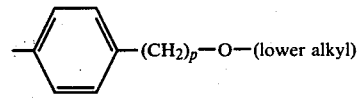

wherein p is 2 or 3 and lower alkyl contains up to 4 carbon atoms. A can also represent a bicyclic aromatic group such as naphthyl or indenyl, or similar groups which are partially saturated or contain substituents. Examples of such similar groups are tetrahydronaphthyl, 1-oxo-1,2,3,4-tetrahydro-5-naphthyl, or 2,3-dihydroxy-1,2,3,4-tetrahydro-5-naphthyl. In addition, A can represent a bicyclic or tricyclic heteroaromatic group such as indolyl, 2-methylindolyl, 3,4-dihydro-2(1H)-qinolinon-5-yl 5-methylcoumarinyl, and 4-hydroxy-5H-furo[3,2g][1]benzopyran-5-onyl. Also, A can represent a monocyclic heterocycle such as cyanopyridyl, carboxypyridyl, carbamoylpyridyl, alkoxycarbonylpyridyl, thiazolyl or 4-morpholino-1,2,5-thiadiazolyl.

Preferred groups for A are o-tolyl, 2-allylphenyl, 2-trifluoromethylphenyl, 2-halo-phenyl, 4-hydroxyphenyl, 2-cyanophenyl, 3-cyanopyridyl, 4-(carbamoylmethyl)phenyl, 4-[(lower alkyl)carboxamido]phenyl, 4-[(lower alkyl)oxyalkyl]phenyl, 2-acetyl-4-butyramidophenyl, 4-(2-acetamidoethyl)phenyl, indol-4-yl, 2-methylindol-4-yl, 2-thiazolyl, and 4-morpholino-1,2,5-thiadiazol-3-yl. Of these, particularly preferred groups are o-tolyl, 2-trifluoromethylphenyl, 2-chlorophenyl, 2-cyanophenyl, 3-cyanopyridyl, 4-(carbamoylmethyl)phenyl, 4-acetamidophenyl, 4-(2- methoxyethyl)phenyl, 2-acetyl-4-butyramidophenyl, and 4-(2-acetamidoethyl)phenyl. The most preferred A groups are o-tolyl, 3-cyanopyridyl, 2-trifluoromethylphenyl, 4-(carbamoylmethyl)phenyl and 4-acetamidophenyl.

The acyl groups encompassed by R are lower alkanoyl containing up to 6 carbon atoms, carboxy(lower alkanoyl) containing up to 4 carbon atoms, carboxyacryloyl, benzoyl, toluoyl, and phenyl(lower alkanoyl) wherein the lower alkanoyl portion contains up to 4 carbon atoms. Examples of specific acyl groups are acetyl, propionyl, butyryl, isobutyryl, pentanoyl, isopentanoyl, pivaloyl, 3-carboxypropionyl, 3-carboxyacryloyl, benzoyl; o-, m- and p-toluoyl; and phenylacetyl. The preferred compounds are those in which R is hydrogen. A preferred acyl group for R is pivaloyl.

Equivalent for the purposes of this invention are the acid addition salts of the above amines with pharmacologically acceptable acids. Useful acids for this purpose include inorganic acids such as hydrochloric, hydrobromic, sulfuric or phosphoric and organic acids such as acetic, propionic, benzoic, naphthoic, oxalic, succinic, maleic, malic, adipic, lactic, tartaric, citric, salicylic, methanesulfonic and p-toluenesulfonic.

It is to be understood that the definition of the compounds above encompasses all possible stereoisomers thereof and mixtures thereof, which possess the activity discussed below, and in particular it encompasses racemic modifications and any optical isomers which possess the indicated activity. In all of the compounds of this invention, the carbinol carbon of the 2-hydroxypropyl group is asymmetric so that at least one pair of optical isomers is possible. If an asymmetric center is also present in Alk or elsewhere in the molecule, additional optical isomers are possible. The individual optical isomers can be obtained from a racemic modification by standard procedures such as forming a salt with an optically active acid followed by crystallization. Where more than one racemic modification is possible for a compound, they can be separated by the usual methods such as chromatography or crystallization. When crystallization is used, it is frequently done after conversion to a salt with an acid that is not optically active. Alternatively, it is possible to obtain optically active products by the use of optically active starting materials in an appropriate procedure described below.

The present compounds are β-adrenergic blocking agents, and thus they are useful in the treatment of cardiovascular diseases such as hypertension, angina pectoris and cardiac arrhythmias. In addition, such β-adrenergic blocking agents are useful in the treatment of glaucoma. Certain of the compounds of this invention show a greater degree of specificity in blocking the cardiac β-receptors than the β-receptors in peripheral blood vessels and bronchial muscle so that they are cardioselective β-adrenergic blocking agents. Such compounds are thus advantageous because the incidence of bronchospasm and peripheral vasoconstriction as side effects would be reduced. The pharmacological action produced by certain of the compounds is further long in duration so that it would be possible to obtain the effects desired with less frequent administration than is possible with other similar agents.

The β-adrenergic blocking activity of the present compounds is demonstrated by their ability to inhibit the isoproterenol-induced increase in heart rate in anesthetized dogs. More specifically, the activity is demonstrated by the ability of the compounds to produce a 50% inhibition of the increased heart rate and the compounds N-[3-(3-cyano-2-pyridyloxy)-2-hydroxypropyl]-1H-benzimidazole-1-propanamine, N-{3-[4-(2-amino-2-oxoethyl)-phenoxy]-2-hydroxypropyl}benzimidazole-1-propanamine, N-{3-[4-(2-amino-2-oxoethyl)phenoxy]2-hydroxypropyl}benzimidazole-1-butanamine and N-{3-[4-(2-methoxyethyl)phenoxy]-2-hydroxypropyl}-1H-benzimidazole-1-propanamine produce such an effect at a dose of 35 µg/kg or less intravenously.

The dosage of the novel compounds of the present invention depends on the age, weight and condition of the individual being treated. Generally speaking, for adult oral administration, the preferred unit dosage of active compound for prophylactic use with suitable pharmaceutical diluent or lubricant is 1.0 to 40 mg, either as tablets, capsules or oral solutions. The intravenous dosage, in sterile aqueous solution for acute use, is 0.1 to 1.0 mg/ml. More specifically, a compound such as N-{3-[4-(2-amino-2-oxoethyl)phenoxy]-2-hydroxypropyl}benzimidazole-1-propanamine would be prepared in tablets containing 10 mg or in aqueous solutions containing 0.25 mg/ml. For the treatment of hypertension, the indicated compound would be administered twice daily at a total dose of 40–160 mg/day; for the treatment of angina, once or twice daily for a total dose of 40 mg/day; for the treatment of arrhythmias, once or twice daily for a total dose of 8–30 mg/day.

For preparing therapeutic compositions such as tablets and other compressed formulations, the compounds can include any compatible and edible tableting material used in pharmaceutical practice as for example, corn starch, lactose, stearic acid, magnesium stearate, talc, methyl cellulose, and the like.

Similarly, the compounds of the present invention can be mixed with suitable adjuvants for the preparation of resorbable hard gelatin or soft capsules utilizing conventional pharmaceutical practices.

The compounds of the present invention can be prepared by a number of different methods. In one method, an aminoalkyl compound of the formula Z-Alk-NH$_2$ is reacted with an epoxide at the formula

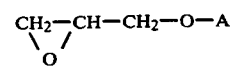

or with a haloalkanol of the formula

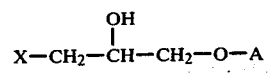

wherein Z, Alk and A are defined as above and X is halogen, preferably chlorine or bromine. X can also represent a reactive ester group such as methylsulfonyloxy. When equivalent quantities of the reactants are used, considerable bis-alkylation of the amine takes place and the presence of the resulting bis-product complicates the isolation of the desired product. The amount of bis-alkylation which takes place can be reduced by using an excess of the amine but this is usually not a desirable procedure when the amine is expensive.

In an alternate procedure, a haloalkyl compound of the formula Z-Alk-X is reacted with an aminopropanol of the formula

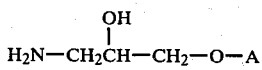

wherein Z, Alk, X and A are defined as above.

The intermediate epoxides are available from the reaction of the appropriate phenol with epichlorohydrin by standare procedures. If desired, the reaction can also be carried out to give the corresponding chlorohydrin which can be used as such or converted to the epoxide by standard procedures.

The intermediate aminoalkylimidazoles (Z-Alk-NH$_2$) are available by the catalytic hydrogenation of the appropriate cyanoalkyl compounds which can be obtained from the imidazole by reaction with compounds such as 2-chloroacetonitrile, acrylonitrile or 4-chlorobutyronitrile, depending on the product desired. The aminoethyl compound can also be obtained by the reaction of the imidazole with acrylamide to give imidazolepropionamide followed by reaction with sodium hypobromite in a Hofmann rearrangement to give the amine as described by W. B. Wheatley and G. F. Stiner, *J. Org. Chem.* 22, 923 (1957).

An alternative procedure for the preparation of the aminoalkylimidazoles involves the reaction of an imidazole with an N-(bromoalkyl)phthalimide to give a compound of the formula

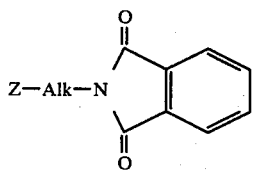

This can then be hydrolyzed or treated with hydrazine to give the desired amine.

The compounds in which R is an acyl group are obtained by the reaction of the appropriate alcohol with an acid halide or acid anhydride with the anhydride being used in the case where R is part of a dicarboxylic acid. The acylation is usually carried out in a diluent or solvent and this can be an excess of the acid halide or acid anhydride used if it is a liquid or it can be the acid corresponding to the anhydride if that acid is a liquid.

In those instances wherein the moiety A in the final product is carboxypyridyl or carbamoylpyridyl or alkoxycarbonylpyridyl or hydroxyphenyl, several ancillary reactions known in the art must be employed. For example, in order to produce a product with A as carboxypyridyl, it is necessary to first obtain the cyanopyridyl compound and subsequently hydrolyse (acid or base) the cyano group to the carboxy group. If on the other hand the carbamoylpyridyl group is desired, then the cyanopyridyl group must be partially hydrolysed. Further, if the compound wherein A is alkoxycarbonylpyridyl (e.g. ethoxycarbonylpyridyl) is to be prepared, then the carboxypyridyl is esterified or the cyanopyridyl compound is treated with acidic catalyst and ethanol. The preparation of the compound wherein A is hydroxyphenyl requires that the corresponding epoxide be prepared with a mono protected benzenediol. Deprotection of the phenylhydroxyl group becomes the last step in the preparation of the final product.

The following examples are presented to illustrate the practice of this invention without limiting its scope.

EXAMPLE 1

A mixture of 15.8 grams of 1H-benzimidazole, 8 grams of acrylonitrile and 0.2 ml of benzyltrimethylammonium hydroxide (40% solution in methanol) in 200 ml of dioxane was stirred at room temperature for 24 hours. The solvent was evaporated from the resulting yellow solution under reduced pressure and the residual yellow solid was triturated first with ether and then with water to give 1H-benzimidazole-1-propionitrile melting at about 108°-110° C.

4.2 Grams of 1H-benzimidazole-1-propionitrile, 0.2 grams sodium hydroxide, 1 gram of Raney nickel catalyst in about 100 ml of ethanol was hydrogenated at room temperature and atmospheric pressure for about 20 hours. The hydrogen uptake had stopped by this time with a total uptake of about 1300 ml. The reaction mixture was filtered and the catalyst was washed first with ethanol and then with water. The filtrates were combined and the solvent evaporated to leave a yellowish oil. The oil was dissolved in water, the water was saturated with sodium chloride, and the mixture was extracted with three portions of methylene chloride. The methylene chloride extracts were combined, washed with sodium chloride solution and then dried over potassium carbonate. The mixture was then filtered and the solvent evaporated to leave a yellowish oil which was then distilled to give 1H-benzimidazole-1-propanamine boiling at 167°-170° C. at 1-1.3 mm pressure.

When the above procedure was repeated using the appropriate imidazole and acrylonitrile to give the corresponding propionitrile followed by hydrogenation over Raney nickel to reduce the nitrile group to an amine, the following compounds were obtained:

2-Methyl-1H-benzimidazole-1-propanamine. In this case, the reduction was completed in a Parr hydrogenation apparatus and the crude oily product was dissolved in chloroform, washed with water, dried over magnesium sulfate and then distilled to give the product boiling at about 168° C. at 0.8 mm pressure.

5-Methyl-1H-benzimidazole-1-propanamine.
4,5,6,7-Tetrahydro-1H-benzimidazole-1propanamine.
1H-Imidazo[4,5-b]pyridine-1-propanamine.
1H-Imidazo[4,5-c]pyridine-1-propanamine.
9H-Purine-9-propanamine.

EXAMPLE 2

To a suspension of 23.6 grams of benzimidazole in 300 ml of dioxane was added 9.8 grams of a 50% dispersion of sodium hydride in mineral oil and the resulting mixture was stirred at room temperature for two hours. A solution of 20.7 grams of 4-chlorobutyronitrile in 100 ml of dioxane was added and the mixture was refluxed for 5 hours. Then, an additional 3 grams of sodium hydride suspension was added and the mixture was refluxed for 17 hours. The mixture was then filtered, concentrated, and washed with petroleum ether to remove the mineral oil. The residual brown oil was then chromatographed on silica gel packed with chloroform and eluted with chloroform and chloroform containing increasing quantities of methanol. The fractions eluted with 0.5% and 1% methanol were combined and the solvent was evaporated to leave residual crude 1H-benzimidazole-1-butanenitrile.

A solution was prepared from 8.9 grams of the nitrile and 150 ml of absolute ethanol, 0.8 grams of palladium on charcoal and 8 ml of concentrated hydrochloric acid were added, and the resulting mixture was hydrogenated at room temperature and pressure for 48 hours. The reaction mixture was then filtered, the solvent was evaporated from the filtrate, and the residue was treated with aqueous 2 N sodium hydroxide solution and extracted with chloroform. The chloroform solution was dried and then distilled to give 1H-benzimidazole-1-butanamine boiling at about 180°–186° C. at 1.2 mm pressure.

EXAMPLE 3

A mixture of 4.84 grams of 1H-benzimidazole-1-ethanamine and 6.22 grams of 1-[4-(2-amino-2-oxoethyl)phenoxy]-2,3-epoxypropane in 100 ml of 95% methanol was refluxed for 22 hours. The solvent was then evaporated from the mixture and the residual solid was triturated with ether three times to give an off-white solid. This was chromatographed on a silica gel column using methanol. The fractions obtained were examined by thin-layer chromatography, the fraction containing the desired product was set aside, and the impure fractions were combined and chromatographed again on silica gel using methanol. The samples containing essentially pure desired product were combined with the earlier product fraction and recrystallized from 2-propanol to give, after drying at 40° C. in vacuo, N-{3-[4-(2-amino-2-oxoethyl)phenoxy]-2-hydroxypropyl}-1H-benzimidazole-1-ethanamine as an off-white solid melting at about 139°–142° C. This compound has the following structural formula:

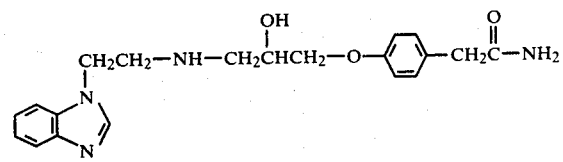

EXAMPLE 4

A mixture of 9.8 grams of 1H-benzimidazole-1-propanamine and 12.16 grams of 1-[4-(2-amino-2-oxoethyl)phenoxy]-2,3-epoxypropane in 400 ml of 95% methanol was refluxed for 17 hours. The solvent was then evaporated under reduced pressure and the residue was chromatographed on a silica gel column packed in chloroform and eluted with solutions containing increasing percentages of methanol in chloroform. The fractions eluted with 30% methanol were combined and the solvent evaporated under reduced pressure. The solid residue was triturated with ether and then separated and dried at reduced pressure and room temperature to give N-{3-[4-(2-amino-2-oxoethyl)phenoxy]-2-hydroxypropyl}-1H-benzimidazole-1-propanamine melting at about 92°–96° C. This compound has the following structural formula:

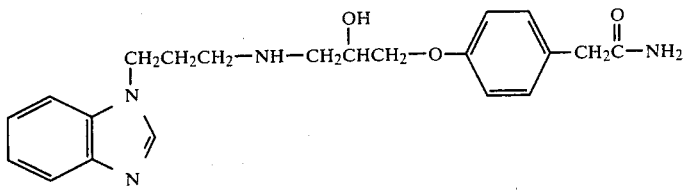

EXAMPLE 5

A mixture of 2.84 grams of 1H-benzimidazole-1-butanamine and 3.11 grams of 1-[4-(2-amino-2-oxoethyl)phenoxy]-2,3-epoxypropane in 50 ml of 90% methanol was heated at reflux for 22 hours. The solvent was evaporated and the residue was triturated with ether to give an off-white solid. This was chromatographed on a silica gel column using methanol. The fractions containing the desired product were determined by thin-layer chromatography and combined. The solvent was then evaporated to give N-{3-[4-(2-amino-2-oxoethyl)phenoxy]-2-hydroxypropyl}-1H-benzimidazole-1-butanamine as an off-white solid melting at about 119°–123° C. This compound has the following structural formula:

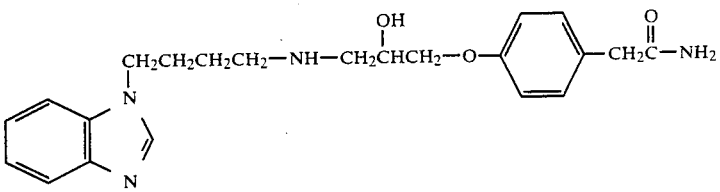

EXAMPLE 6

A mixture of 4.16 grams of 2-methyl-1H-benzimidazole-1-propanamine and 4.56 grams of 1-[4-(2-amino-2-oxoethyl)phenoxy]-2,3-epoxypropane in 50 ml of 90% methanol was refluxed for 22 hours. The solvent was then evaporated to leave a thick oil which was chromatographed on a silica gel column using methanol. The fractions containing the desired product were determined by thin-layer chromatography and combined. The solvent was evaporated to leave a thick oily residue which solidified partially on standing. This was recrystallized from ethanol to give N-{3-[4-(2-amino-2-oxoethyl)phenoxy]-2-hydroxypropyl}-2-methyl-1H-benzimidazole-1-propanamine melting at about 146°–149° C. This compound has the following structural formula:

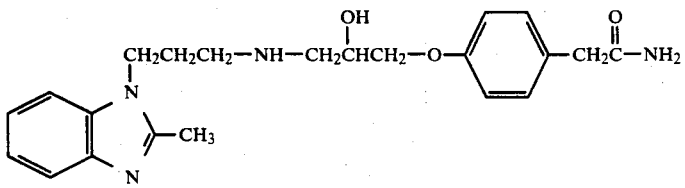

EXAMPLE 7

5.25 Grams of 1H-benzimidazole-1-propanamine, 6.5 grams of 1-(4-acetamidophenoxy)-2,3-epoxypropane and 10 ml of 95% methanol were combined and refluxed for about 55 hours. The solvent was then evaporated under reduced pressure and the residual oil was chromatographed on a silica gel column using methanol. The fractions obtained were examined by thin-layer chromatography and the fractions containing the desired product were combined and chromatographed again on silica gel using methanol. The fractions containing the pure product were combined and the solvent was evaporated under reduced pressure to leave a residual waxy solid. This was dried under vacuum at room temperature to give N-[3-(4-acetamidophenoxy)-2-hydroxypropyl]-1H-benzimidazole-1-propanamine methanolate melting at about 59°–65° C. The free amine has the following structural formula:

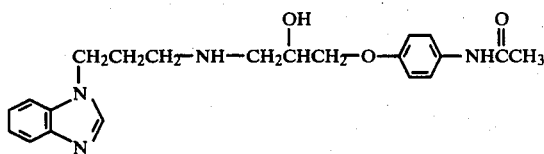

EXAMPLE 8

A mixture of 3.5 grams of 1H-benzimidazole-1-propanamine and 3.8 grams of 1-[4-(2-methoxyethyl)-phenoxy]-2,3-epoxypropane in 2 ml of 90% methanol was stirred at room temperature for 64 hours. The solvent was then evaporated under reduced pressure and the residue was chromatographed on a silica gel column using methanol. The fractions obtained were examined by thin-layer chromatography, and the fractions containing the desired product were combined. The solvent was evaporated and the residue was dried under vacuum at room temperature to give N-{3-[4-(2-methoxyethyl)phenoxy]-2-hydroxypropyl}-1H-benzimidazole-1-propanamine hydrate as a yellow oil. The free base has the following structural formula:

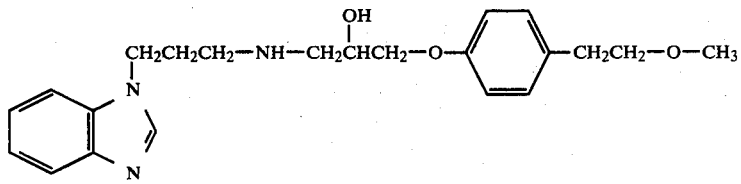

EXAMPLE 9

When 1-[4-(2-amino-2-oxoethyl)phenoxy]-2,3-epoxypropane was reacted with the appropriate substituted propanamine or other appropriate amine according to the procedure described in Example 4 and the crude product was then purified by chromatography, the following products were obtained:

N-{3-[4-(2-amino-2-oxoethyl)phenoxy]-2-hydroxypropyl}-5-methyl-1H-benzimidazole-1-propanamine N-{3-[4-(2-amino-2-oxoethyl)phenoxy]-2-hydroxypropyl}-4,5,6,7-tetrahydro-1H-benzimidazole-1-propanamine N-{3-[4-(2-amino-2-oxoethyl)phenoxy]-2-hydroxypropyl}-1H-imidazo[4,5-b]pyridine-1-propanamine N-{3-[4-(2-amino-2-oxoethyl)phenoxy]-2-hydroxypropyl}-1H-imidazo[4,5-c]pyridine-1-propanamine N-{3-[4-(2-amino-2-oxoethyl)phenoxy]-2-hydroxypropyl}-9H-purine-9-propanamine N-{3-[4-(2-amino-2-oxoethyl)phenoxy]-2-hydroxypropyl}-α-methyl-1H-benzimidazole-1-ethanamine N-{3-[4-(2-amino-2-oxoethyl)phenoxy]-2-hydroxypropyl}-1H-benzimidazole-1-pentanamine.

In this case, the 1H-benzimidazole-1-pentanamine used as the starting material was obtained by first reacting N-(5-bromopentyl)phthalimide with 1H-benzimidazole to give 1-(5-phthalimidopentyl)-1H-benzimidazole which was then treated with hydrazine to give the amine, all according to general procedures known in the art (Houben-Weyl, Vol. XI/1, page 82, George Thieme Verlag, Stuttgart, 1957).

EXAMPLE 10

When 1H-benzimidazole-1-propanamine or other appropriate amine was reacted with the appropriate substituted 1-phenoxy-2,3-epoxypropane according to the procedure described in Example 4 and the crude product obtained was purified by chromatography, or subsequently deprotected and then purified, the following compounds were obtained:

N-(3-phenoxy-2-hydroxypropyl)-1H-benzimidazole-1-propanamine

N-[3-(2-methylphenoxy)-2-hydroxypropyl]-1H-benzimidazole-1-propanamine

N-[3-(2-cyanophenoxy)-2-hydroxypropyl]-1H-benzimidazole-1-propanamine

N-[3-(2-cyclopentylphenoxy)-2-hydroxypropyl]-1H-benzimidazole-1-propanamine

N-[3-(2-allylphenoxy)-2-hydroxypropyl]-1H-benzimidazole-1-propanamine

N-[3-(2-allyloxyphenoxy)-2-hydroxypropyl]-1H-benzimidazole-1-propanamine

N-[3-(3,5-dimethoxyphenoxy)-2-hydroxypropyl]-1H-benzimidazole-1-propanamine

N-{3-[4-(2-ethoxyethyl)phenoxy]-2-hydroxypropyl}-1H-benzimidazole-1-propanamine

N-{3-[4-(3-methoxypropyl)phenoxy]-2-hydroxypropyl}-1H-benzimidazole-1-propanamine N-[3-(4-hydroxyphenoxy)-2-hydroxypropyl]-1H-benzimidazole-1-propanamine N-[3-(2-cyanophenoxy)-2-hydroxypropyl]-1H-benzimidazole-1-propanamine N-[3-(2-nitrophenoxy)-2-hydroxypropyl]-1H-benzimidazole-1-propanamine N-[3-(2-chlorophenoxy)-2-hydroxypropyl]-1H-benzimidazole-1-propanamine N-[3-(2-trifluoromethylphenoxy)-2-hydroxypropyl]-1H-benzimidazole-1-propanamine N-[3-(4-hydroxyphenoxy)-2-hydroxypropyl]-1H-benzimidazole-1-butanamine.

EXAMPLE 11

When 1H-benzimidazole-1-propanamine was reacted with the appropriate aminosubstituted 1-phenoxy-2,3-epoxypropane according to the procedure described in Example 4 and the crude product obtained was purified by chromatography, the following compounds were obtained:

N-[3-(4-butyramidophenoxy)-2-hydroxypropyl]-1H-benzimidazole-1-propanamine

N-[3-(4-acetamido-3-methylphenoxy)-2-hydroxypropyl]-1H-benzimidazole-1-propanamine N-[3-(4-acetamido-2-chlorophenoxy)-2-hydroxypropyl]-1H-benzimidazole-1-propanamine N-{3-[4-(2-acetamidoethyl)phenoxy]-2-hydroxypropyl}-1H-benzimidazole-1-propanamine N-{3-[4-(acetamidomethyl)-2-methylphenoxy]-2-hydroxypropyl}-1H-benzimidazole-1-propanamine N-{3-[4-(methoxycarbonylamino)phenoxy]-2-hydroxypropyl}-1H-benzimidazole-1-propanamine N-{3-[4-(ethoxycarbonylamino)phenoxy]-2-hydroxypropyl}-1H-benzimidazole-1-propanamine N-[3-(2-acetyl-4-butyramidophenoxy)-2-hydroxypropyl]-1H-benzimidazole-1-propanamine

EXAMPLE 12

When 1H-benzimidazole-1-propanamine was reacted with the appropriate carbamoyl substituted 1-phenoxy-2,3-epoxypropane according to the procedure described in Example 4 and the crude product obtained was purified by chromatography, the compounds listed below were obtained. In each case, the epoxide starting material was obtained by the reaction of the corresponding chlorohydrin with base by standard procedures.

N-{3-[4-(2-methylamino-2-oxoethyl)phenoxy]-2-hydroxypropyl}-1H-benzimidazole-1-propanamine N-{3-[4-(2-butylamino-2-oxoethyl)phenoxy]-2-hydroxypropyl}-1H-benzimidazole-1-propanamine N-{3-[4-(2-amino-2-oxoethyl)-2-methylphenoxy]-2-hydroxypropyl}-1H-benzimidazole-1-propanamine N-{3-[4-(2-amino-2-oxoethyl)-2-bromophenoxy]-2-hydroxypropyl}-1H-benzimidazole-1-propanamine

EXAMPLE 13

When 1H-benzimidazole-1-propanamine was reacted with the appropriate 1-aryloxy-2,3-epoxypropane according to the procedure described in Example 4 and the crude product obtained was purified by chromatography, the following compounds were obtained:

N-[3-(4-indenyloxy)-2-hydroxypropyl]-1H-benzimidazole-1-propanamine

N-[3-(1-naphthyloxy)-2-hydroxypropyl]-1H-benzimidazole-1-propanamine

N-[3-(1,2,3,4-tetrahydro-6-naphthyloxy)-2-hydroxypropyl]-1H-benzimidazole-1-propanamine N-[3-(1-oxo-1,2,3,4-tetrahydro-5-naphthyloxy)-2-hydroxypropyl]-1H-benzimidazole-1-propanamine N-[3-(2,3-dihydroxy-1,2,3,4-tetrahydro-5-naphthyloxy)-2-hydroxypropyl]-1H-benzimidazole-1-propanamine

EXAMPLE 14

When 1H-benzimidazole-1-propanamine or other appropriate amine was reacted with the appropriate 1-[(heterocyclic)oxy]-2,3-epoxypropane according to the procedure described in Example 4 and the crude product was purified by chromatography, or subsequently reacted and then purified, the following compounds were obtained:

N-[3-(4-indolyloxy)-2-hydroxypropyl]-1H-benzimidazole-1-propanamine

N-[3-(2-methyl-4-indolyloxy)-2-hydroxypropyl]-1H-benzimidazole-1-propanamine

5-{3-[3-(1H-benzimidazol-1-yl)propylamino]-2-hydroxypropoxy}-3,4-dihydro-2(1H)-quinolinone 8-{3-[3-(1H-benzimidazol-1-yl)propylamino]-2-hydroxypropoxy}-5-methylcoumarin N-[3-(2-thiazolyloxy)-2-hydroxypropyl]-1H-benzimidazole-1-propanamine N-{3-[(4-morpholino-1,2,5-thiadiazol-3-yl)oxy]-2-hydroxypropyl}-1H-benzimidazole-1-propanamine N-[3-(3-cyano-2-pyridyloxy)-2-hydroxypropyl]-1H-benzimidazole-1-propanamine N-[3-(3-carboxy-2-pyridyloxy)-2-hydroxypropyl]-1H-benzimidazole-1-propanamine N-[3-(3-carbamoyl-2-pyridyloxy)-2-hydroxypropyl]-1H-benzimidazole-1-propanamine N-[3-(3-ethoxycarbonyl-2-pyridyloxy)-2-hydroxypropyl]-1H-benzimidazole-1-propanamine N-[3-(3-cyano-2-pyridyloxy)-2-hydroxypropyl]-α-methyl-1H-benzimidazole-1-propanamine N-[3-(3-cyano-2-pyridyloxy)-2-hydroxypropyl]-1H-benzimidazole-1-butanamine N[3-(3-cyano-2-pyridyloxy)-2-hydroxypropyl]-1H-benzimidazole-1-ethanamine.

EXAMPLE 15

A mixture of 3.2 grams of N-{3-[4-(2-amino-2-oxoethyl)phenoxy]-2-hydroxypropyl}-1H-benzimidazole-1-propanamine and 4.82 grams of pivaloyl chloride in 40 ml of trifluoroacetic acid was stirred at room temperature for 40 minutes. The solvent was then evaporated and the residue was triturated with ether and then mixed with aqueous sodium bicarbonate solution and chloroform until it dissolved. The chloroform layer was separated and dried over magnesium sulfate and the solvent evaporated to leave a brown oil. This was then chromatographed on a silica gel column using methanol. The fractions containing the desired product were combined and the solvent was evaporated. 2.4 Grams of the residue was dissolved in methanol and mixed with 0.64 grams of oxalic acid dihydrate in methanol. Ether was added and the precipitate which formed was separated by filtration after the mixture was cooled. The solid was washed with ether and dried under reduced pressure to give N-{3-[4-(2-amino-2-oxoethyl)phenoxy]-2-(trimethylacetoxy)propyl}-1H-benzimidazole-1-propanamine as the oxalic acid salt monohydrate. The free base of this compound has the following structural formula:

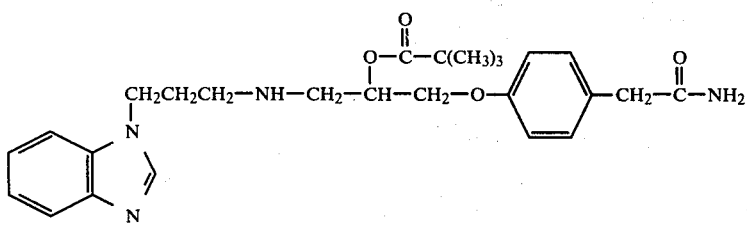

EXAMPLE 16

A mixture of 47.3 grams of 1H-benzimidazole, 33.6 grams of 3-buten-2-one and 16 ml. of triethylamine in 400 ml. of methanol was heated slowly to 41° C. and maintained at that temperature for about 4.5 hours. More 3-buten-2-one was added (about 1 ml.) and heating was continued at 45° C. for 17 hours. The mixture was then cooled and filtered to remove some precipitate before it was poured into 2400 ml. of water and cooled further. Some additional precipitate was removed by filtration and the solvent was evaporated from the filtrate to leave a brown oil which was crude 1-(3-oxobutyl)-1H-benzimidazole. This material was sufficiently pure for use in the next reaction.

A mixture of 7.0 grams of 1-(3-oxobutyl)-1H-benzimidazole, 28.7 grams of ammonium acetate and 1.6 grams of sodium cyanoborohydride in 100 ml. of methanol was stirred at room temperature for about 24 hours. The mixture was then acidified with about 40 ml. of concentrated hydrochloric acid and the solvent was evaporated. The residue was dissolved in 150 ml. of water and the aqueous solution was extracted first with ether and then it was made alkaline (pH greater than 10) with solid potassium hydroxide. The alkaline solution was extracted with several portions of methylene chloride and the organic extracts were combined, washed with water and dried over magnesium sulfate and the methylene chloride was evaporated. The residue was chromatographed on a silica gel column packed in acetonitrile and eluted with acetonitrile and acetonitrile containing increasing percentages of methanol. The fractions containing the desired product, as determined by thin-layer chromatography, were combined and the solvent evaporated to give α-methyl-1H-benzimidazole-1-propanamine as an oil.

A mixture of 1.65 grams of α-methyl-1H-benzimidazole-1-propanamine and 1.82 grams of 1-[4-(2-amino-2-oxoethyl)phenoxy]-2,3-epoxypropane in 6 ml. of 95 percent methanol was refluxed for 19 hours. The solvent was evaporated from the mixture and the residual solid was triturated several times with ether. The solid was then dried and chromatographed on a silica gel column using methanol. The fractions containing the desired product were determined by thin-layer chromatography and combined. The solvent was then evaporated to leave a residual oil which solidified on cooling to give N-{3-[4-(2-amino-2-oxoethyl)phenoxy]-2-hydroxypropyl}-α-methyl-1H-benzimidazole-1-propanamine melting at about 139°-142° C. This compound has the following structural formula.

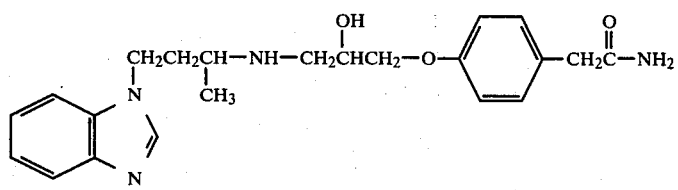

EXAMPLE 17

0.5 Gram of 10% palladium on charcoal was prehydrogenated in 100 ml. of absolute ethanol until the uptake of hydrogen stopped. Then, a solution of 10 grams of 1H-benzimidazole-1-propanamine and 6.7 grams of benzaldehyde in 50 ml. of absolute ethanol was added and the mixture was stirred at atmospheric pressure and room temperature under hydrogen until the calculated amount of hydrogen was taken up. The catalyst was then removed by filtration and the solvent was evaporated to leave N-benzyl-1H-benzimidazole-1-propanamine as a colorless oil. This material was sufficiently pure for further reaction but, if desired, a pure sample could be obtained by column chromatography on silica gel.

A mixture of 570 milligrams of N-benzyl-1H-benzimidazole-1-propanamine and 445 milligrams of 1-[4-(2-amino-2-oxoethyl)phenoxy]-2,3-epoxypropane in 6 ml. of 95% methanol was refluxed for 16 hours. The solvent was then evaporated and the residue was chromatographed on a silica gel column using methanol. The fractions obtained were examined by thin layer chromatography and the fractions containing the desired product were combined. The solvent was evaporated from the combined fractions to give, as a residue, N-benzyl-N-{3-[4-(2-amino-2-oxoethyl)phenoxy]-2-hydroxypropyl}-1H-benzimidazole-1-propanamine.

A mixture of 0.5 gram of N-benzyl-N-{3-[4-(2-amino-2-oxoethyl)phenoxy]-2-hydroxypropyl}-1H-benzimidazole-1-propanamine and 0.17 gram of 10% palladium on carbon in 30 ml. of glacial acetic acid was hydrogenated for 17 hours at room temperature and an initial pressure of 40 pounds per square inch. The reaction mixture was then filtered and the solvent was evaporated from the filtrate to leave a semi-solid which was N-{3-[4-(2-amino-2-oxoethyl)phenoxy]-2-hydroxypropyl}-1H-benzimidazole-1-propanamine as a salt with acetic acid. This product was mixed with an equivalent of oxalic acid in methanol and the white solid obtained was recrystallized from methanol to give N-{3-[4-(2-amino-2-oxoethyl)phenoxy]-2-hydroxypropyl}-1H-

We claim:
1. A compound of the formula:

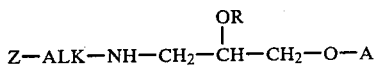

wherein Z is selected from the group consisting of 4,5,6,7-tetrahydro-1-benzimidazolyl, 1H-imidazo[4,5-b]-pyridin-1-yl, 1H-imidazo[4,5-c]pyridin-1-yl and (9H)-9-purinyl; ALK is alkylene containing 2 to 6 carbon atoms; R is selected from the group consisting of hydrogen, lower alkanoyl containing up to 6 carbon atoms, carboxy (lower alkanoyl) containing up to 4 carbon atoms, carboxyacryloyl, benzoyl, toluoyl and phenyl (lower alkanoyl) wherein the lower alkanoyl portion contains up to 4 carbon atoms; and A is selected from the group consisting of phenyl, tolyl, hydroxyphenyl, halophenyl, nitrophenyl, trifluoromethylphenyl, cyanophenyl, cyclopentylphenyl, allylphenyl, allyloxyphenyl, dimethoxyphenyl, carbamoylmethylphenyl of the formula

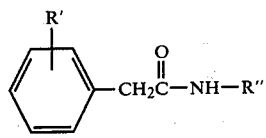

wherein R' is hydrogen, methyl or halogen and R" is hydrogen, lower alkyl containing up to 4 carbon atoms, (acid amido)phenyl and (acid amido alkyl)phenyl of the formula

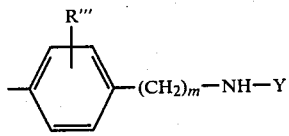

wherein m is 0–2, R''' is hydrogen, methyl, acetyl or halogen and Y is

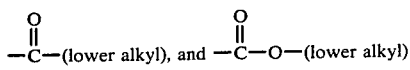

in which lower alkyl contains up to 4 carbon atoms, (lower alkyl)oxyalkylphenyl of the formula

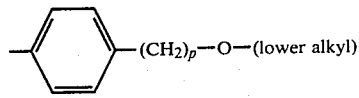

wherein p is 2 or 3 and lower alkyl contains up to 4 carbon atoms; naphthyl, indenyl, tetrahydronaphthyl, 1-oxo-1,2,3,4-tetrahydro-5-naphthyl, 2,3-dihydroxy-1,2,3,4-tetrahydro-5-naphthyl, indolyl, 2-methylindolyl, 3,4-dihydro-2(1H)-quinolinon-5-yl, 5-methylcoumarin-8-yl, cyanopyridyl, carboxypyridyl, carbamoylpyridyl, alkoxycarbonylpyridyl, thiazolyl and 4-morpholino-1,2,5-thiadiazol-3-yl; or a pharmaceutically acceptable acid addition salt thereof.

2. A compound according to claim 1 having the formula

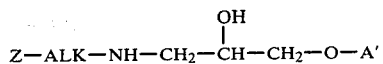

wherein Z is selected from the group consisting of 4,5,6,7-tetrahydro-1-benzimidazolyl, 1H-imidazo[4,5-b]pyridin-1-yl, 1H-imidazo[4,5-c]pyridin-1-yl and (9H)-9-purinyl; ALK is alkylene containing 2 to 6 carbon atoms; and A' is selected from the group consisting of tolyl, allylphenyl, trifluoromethylphenyl, chlorophenyl, cyanophenyl, hydroxyphenyl, nitrophenyl, 4-(carbamoylmethyl)phenyl, 4-[(lower alkyl)carboxamido]phenyl, 4-[(lower alkyl)oxyalkyl]phenyl, 2-acetyl-4-butyramidophenyl, 4-(2-acetamidoethyl)phenyl, indol-4-yl, 2-methylindol-4-yl, 2-thiazolyl, 4-morpholino-1,2,5-thiadiazol-3-yl, cyanopyridyl, carboxypyridyl, carbamoylpyridyl and alkoxycarbonylpyridyl.

3. A compound according to claim 1 having the formula

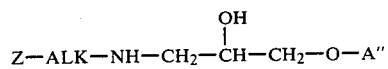

wherein Z is selected from the group consisting of 4,5,6,7-tetrahydro-1-benzimidazolyl, 1H-imidazo[4,5-b]pyridin-1-yl, 1H-imidazo[4,5-c]pyridin-1-yl and (9H)-9-purinyl; ALK is alkylene containing 2 to 6 carbon atoms; and A" is selected from the group consisting of o-tolyl, 2-allylphenyl, 2-trifluoromethylphenyl, 2-nitrophenyl, 2-chlorophenyl, 2-cyanophenyl, 4-hydroxyphenyl, 4-(carbamoylmethyl)phenyl, 4-acetamidophenyl, 4-(2-methoxyethyl)phenyl, 2-acetyl-4-butyramidophenyl, 4-(2-acetamidoethyl)phenyl, 2-thiazolyl, 2-cyanopyridyl, 2-carboxypyridyl, 2-carbamoylpyridyl.

4. A compound according to claim 1 having the formula

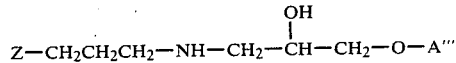

wherein Z is selected from the group consisting of 4,5,6,7-tetrahydro-1-benzimidazolyl, 1H-imidazo[4,5-b]pyridin-1-yl, 1H-imidazo[4,5-c]pyridin-1-yl and (9H)-9-purinyl; and A''' is selected from the group consisting of o-tolyl, 2-allylphenyl, 2-trifluoromethylphenyl, 2-cyanophenyl, 2-nitrophenyl, 2-chlorophenyl, 4-hydroxyphenyl, 4-(carbamoylmethyl)phenyl, 4-acetamidophenyl, 4-(2-methoxyethyl)phenyl, 2-acetyl-4-butyramidophenyl, 4-(2-acetamidoethyl)phenyl, 2-thiazolyl, 3-cyano-2-pyridyl, 3-carboxy-2-pyridyl and 3-carbamoyl-2-pyridyl.

5. A compound according to claim 1 having the formula

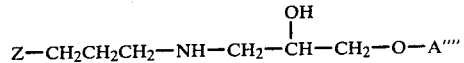

wherein Z is selected from the group consisting of 4,5,6,7-tetrahydro-1-benzimidazolyl, 1H-imidazo[4,5-b]-pyridin-1-yl, 1H-imidazo[4,5-c]pyridin-1-yl and (9H)-9-purinyl; and A'''' is selected from the group consisting of o-tolyl, 2-cyanophenyl, 2-trifluoromethylphenyl, 4-hydroxyphenyl, 4-(carbamoylmethyl)phenyl, 4-acetamidophenyl and 3-cyano-2-pyridyl.

6. A pharmaceutical composition for producing a β-adrenergic blocking effect comprising a non-toxic, β-adrenergic blocking effective amount per unit dosage of a compound of claim 1, together with a non-toxic, pharmaceutically acceptable carrier.

7. The method of effecting β-adrenergic activity in a mammalain host having a condition in which therapeutic benefit is derived from inhibition of the β-adrenergic receptors which comprises administering to said host a non-toxic effective adrenergic β-receptor inhibiting dose of a compound as claimed in claim 1.

* * * * *